United States Patent
Kunz et al.

(10) Patent No.: US 10,456,530 B2
(45) Date of Patent: Oct. 29, 2019

(54) SUPPLEMENTARY DEVICE FOR ATTACHMENT TO A DRUG INJECTION DEVICE FOR MONITORING INJECTION DOSES HAVING OCR IMAGING SYSTEM WITH GLARE REDUCTION

(71) Applicant: SANOFI-AVENTIS DEUTSCHLAND GMBH, Frankfurt am Main (DE)

(72) Inventors: Theresa Kunz, Jena (DE); Mario Bock, Hamburg (DE); Gertrud Blei, Jena (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 190 days.

(21) Appl. No.: 15/515,942

(22) PCT Filed: Oct. 5, 2015

(86) PCT No.: PCT/EP2015/072905
§ 371 (c)(1),
(2) Date: Mar. 30, 2017

(87) PCT Pub. No.: WO2016/055401
PCT Pub. Date: Apr. 14, 2016

(65) Prior Publication Data
US 2017/0312446 A1 Nov. 2, 2017

(30) Foreign Application Priority Data
Oct. 6, 2014 (EP) .................................... 14187695

(51) Int. Cl.
*A61M 5/24* (2006.01)
*A61M 5/315* (2006.01)
(Continued)

(52) U.S. Cl.
CPC .......... *A61M 5/31568* (2013.01); *A61M 5/24* (2013.01); *A61M 5/31525* (2013.01);
(Continued)

(58) Field of Classification Search
CPC .. A61M 2005/3126; A61M 2205/3306; A61M 5/24; A61M 5/31525;
(Continued)

(56) References Cited

U.S. PATENT DOCUMENTS

| 9,317,916 B1* | 4/2016 | Hanina | ................. G06T 7/0012 |
| 2003/0065287 A1* | 4/2003 | Spohn | ............... A61M 5/14566 604/154 |

(Continued)

FOREIGN PATENT DOCUMENTS

WO   WO 2013/120777   8/2013

OTHER PUBLICATIONS

International Preliminary Report on Patentability in International Application No. PCT/EP2015/072905, dated Apr. 11, 2017, 9 pages.
(Continued)

*Primary Examiner* — Eileen M Adams
(74) *Attorney, Agent, or Firm* — Fish & Richardson P.C.

(57) ABSTRACT

The present disclosure relates to a supplementary device for attachment to an injection device including an imaging arrangement configured to capture an image of a moveable number sleeve of the injection device, a plurality of light sources, and a processor arrangement configured to control operation of the imaging arrangement and the plurality of light sources and to receive image data from the imaging arrangement. In some instances, the processor arrangement is configured to activate the plurality of light sources sequentially and to combine multiple images captured by the imaging apparatus under different illumination conditions into a single image.

6 Claims, 7 Drawing Sheets

(51) Int. Cl.
- *G06T 5/50* (2006.01)
- *G06K 9/20* (2006.01)
- *A61M 5/32* (2006.01)
- *G06K 9/34* (2006.01)
- *G06K 9/78* (2006.01)
- *A61M 5/31* (2006.01)

(52) U.S. Cl.
CPC ........... *A61M 5/3202* (2013.01); *G06K 9/209* (2013.01); *G06K 9/2027* (2013.01); *G06K 9/2036* (2013.01); *G06K 9/2054* (2013.01); *G06K 9/344* (2013.01); *G06K 9/78* (2013.01); *G06T 5/50* (2013.01); *A61M 2005/3126* (2013.01); *A61M 2205/3306* (2013.01); *G06K 2209/01* (2013.01); *G06K 2209/03* (2013.01); *G06T 2207/10152* (2013.01); *G06T 2207/20021* (2013.01); *G06T 2207/20221* (2013.01); *G06T 2207/30004* (2013.01); *G06T 2207/30232* (2013.01)

(58) Field of Classification Search
CPC ............ A61M 5/31568; A61M 5/3202; G06K 2209/01; G06K 2209/03; G06K 9/2027; G06K 9/2036; G06K 9/2054; G06K 9/209; G06K 9/344; G06K 9/78; G06T 2207/10152; G06T 2207/20021; G06T 2207/20221; G06T 2207/30004; G06T 2207/30232; G06T 5/50

See application file for complete search history.

(56) References Cited

U.S. PATENT DOCUMENTS

| | | | |
|---|---|---|---|
| 2007/0106306 A1* | 5/2007 | Bodduluri | A61B 17/32053 606/133 |
| 2008/0137208 A1* | 6/2008 | Pochapsky | G02B 27/0101 359/630 |
| 2008/0165266 A1* | 7/2008 | Jenkins | G06F 3/0418 348/333.01 |
| 2009/0073307 A1* | 3/2009 | Kramer | H04N 5/2354 348/370 |
| 2009/0163860 A1* | 6/2009 | Patrick | A61B 8/00 604/83 |
| 2012/0022458 A1* | 1/2012 | Oh | A61M 5/31551 604/189 |
| 2013/0051631 A1* | 2/2013 | Hanna | G06K 9/00604 382/117 |
| 2013/0329073 A1* | 12/2013 | Majewicz | H04N 1/387 348/222.1 |
| 2014/0194826 A1* | 7/2014 | Nielsen | A61M 5/24 604/189 |
| 2014/0249410 A1* | 9/2014 | Uber, III | A61M 5/31573 600/432 |
| 2014/0276213 A1* | 9/2014 | Bochenko | A61M 39/0208 600/573 |

OTHER PUBLICATIONS

International Search Report and Written Opinion in International Application No. PCT/EP2015/072905, dated Dec. 1, 2015, 13 pages.

\* cited by examiner

SUPPLEMENTARY DEVICE FOR ATTACHMENT TO A DRUG INJECTION DEVICE FOR MONITORING INJECTION DOSES HAVING OCR IMAGING SYSTEM WITH GLARE REDUCTION

CROSS-REFERENCE TO RELATED APPLICATIONS

This application is a U.S. national stage application under 35 USC § 371 of International Application No. PCT/EP2015/072905, filed on Oct. 5, 2015, which claims priority to European Patent Application No. 14187695.3 filed on Oct. 6, 2014, the entire contents of which are incorporated herein by reference.

TECHNICAL FIELD

Certain aspects of the present disclosure relates to a supplementary device for attachment to an injection device, and in particular to a supplementary device comprising a processor arrangement configured to activate a plurality of light sources sequentially and to combine into a single image multiple images captured by an imaging apparatus under different illumination conditions.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

SUMMARY

A first aspect of the disclosure provides a supplementary device for attachment to an injection device, the supplementary device comprising:
an imaging arrangement configured to capture an image of a moveable number sleeve of the injection device;
a plurality of light sources; and
a processor arrangement configured to control operation of the imaging arrangement and plurality of light sources and to receive image data from the imaging arrangement,
wherein the processor arrangement is configured to activate the plurality of light sources sequentially and to combine multiple images captured by the imaging apparatus under different illumination conditions into a single image.

The processor may be configured to divide a field of view of the imaging arrangement into a plurality of areas and to associate each of the areas with a respective illumination condition. The processor arrangement may be configured to combine multiple images captured by the imaging apparatus under different illumination conditions into a single image by being configured to combine an image of a first area of the plurality of areas captured under a first illumination condition with an image of a second area of the plurality of areas captured under a second illumination condition.

The supplementary device may comprise four light sources grouped into first and second pairs and may be configured to activate the plurality of light sources sequentially by being configured to activate the first pair of light sources followed by the second pair of light sources.

The processor may be configured to control the imaging arrangement to:
capture a first image of the number sleeve when the first pair of light sources are activated; and
capture a second image of the number sleeve when the second pair of light sources are activated.

The processor may be configured to divide the field of view of the imaging arrangement into first and second halves and to associate the first half with a first illumination condition and the second half with a second illumination condition. The processor may be configured to keep the first half of the first image and discard the second half of the first image and to keep the second half of the second image and discard the first half of the second image. The processor arrangement may be configured to combine multiple images captured by the imaging apparatus under different illumination conditions into a single image by being configured to combine the first half of the first image and the second half of the second image into a single image.

In some other embodiments, the processor may be configured to divide the field of view of the imaging arrangement into a central section and two peripheral sections and to associate the central section with a first illumination condition and the two peripheral sections with a second illumination condition.

Each illumination source, when activated, may result in one or more reflections from a transparent window of the injection device being visible in a field of view of the imaging apparatus.

A second aspect of the disclosure provides a system comprising a supplementary device according to the first aspect of the disclosure and an injection device comprising a moveable number sleeve and being configured to have the supplementary device attached thereto.

A third aspect of the disclosure provides a method of operating a supplementary device for attachment to an injection device, the supplementary device having an imaging arrangement configured to capture an image of a moveable number sleeve of the injection device, a plurality of light sources and a processor arrangement configured to control operation of the imaging arrangement and the plurality of light sources, the method comprising:
activating the plurality of light sources sequentially;
receiving image data from the imaging arrangement; and
combining multiple images captured by the imaging apparatus under different illumination conditions into a single image.

Embodiments of the disclosure will now be described, by way of example only, with reference to the accompanying drawings.

BRIEF DESCRIPTION OF THE FIGURES

The figures show:

FIG. 1b shows a perspective view of some detail of the drug delivery device of FIG. 1a;

FIG. 5b: a final image created by combining partial images of the field of view of FIG. 5a;

DETAILED DESCRIPTION

In the following, embodiments of the present disclosure will be described with reference to an insulin injection device. The present disclosure is however not limited to such application and may equally well be deployed with injection devices that eject other medicaments, or with other types of medical devices.

Figure 1A:
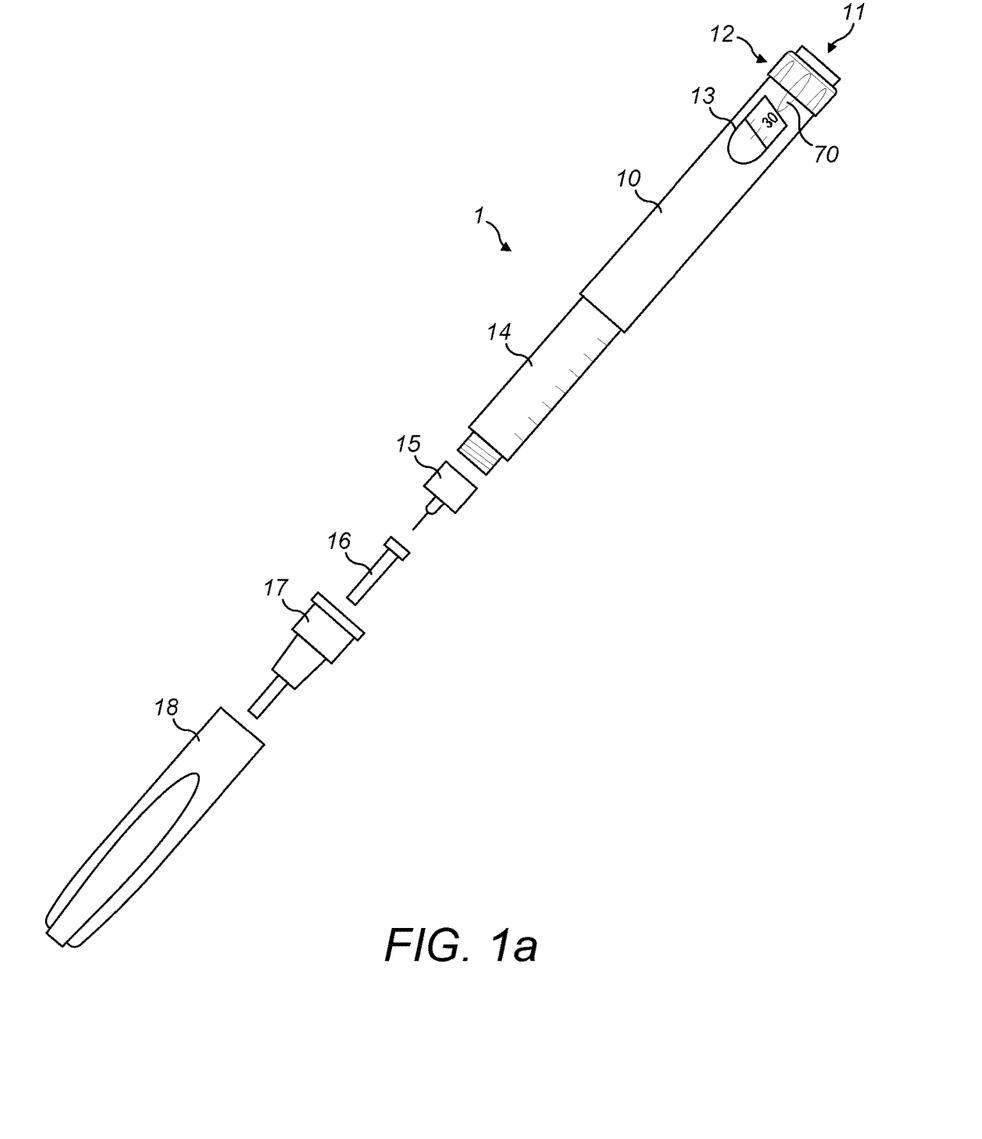
FIG. 1a: an exploded view of an drug delivery device.

FIG. 1 is an exploded view of an injection device 1 (also referred to herein as a drug delivery device 1, injection pen 1 or pen device 1), which may for instance represent Sanofi's Solostar® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently. A label (not shown) is provided on the housing 10. The label includes information about the medicament included within the injection device, including information identifying the medicament. The information identifying the medicament may be in the form of text. The information identifying the medicament may also be in the form of a color. The information identifying the medicament may also be encoded into a barcode, QR code or the like. The information identifying the medicament may also be in the form of a black and white pattern, a color pattern or shading.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
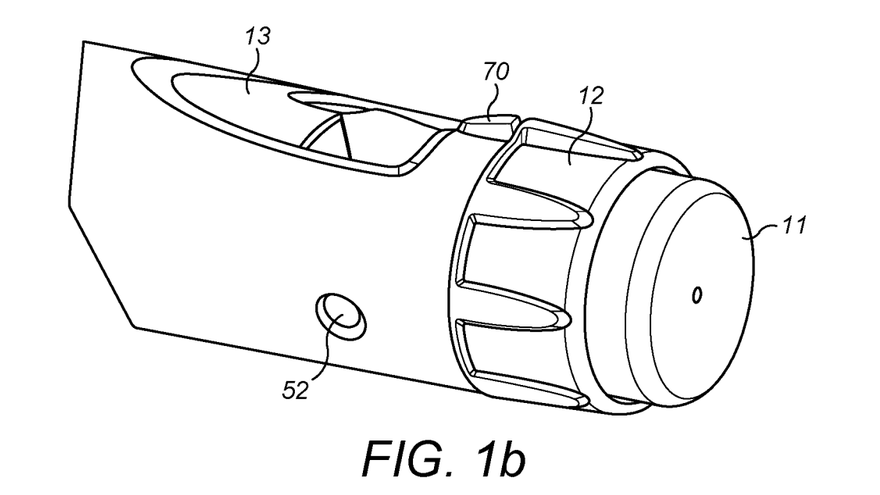

FIG. 1b is a close-up of the end of the injection device 1. This Fig. shows a locating rib 70 that is located between the viewing window 13 and the dosage knob 12.

Figure 2A:
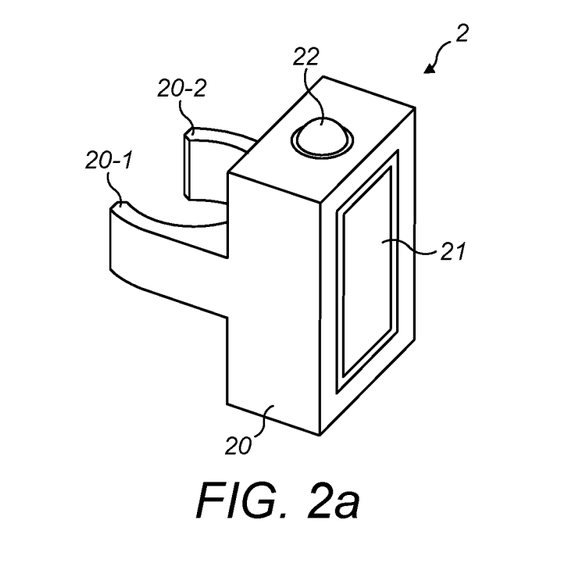
FIG. 2a: a schematic illustration of a supplementary device to be releasably attached to the drug delivery device of FIGS. 1a and 1b according to an aspect of the present disclosure.

FIG. 2a is a schematic illustration of an embodiment of a supplementary device 2 (also referred to herein as an additional device 2, clip-on device 2 or sensor device 2) to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises at least one user input transducer, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
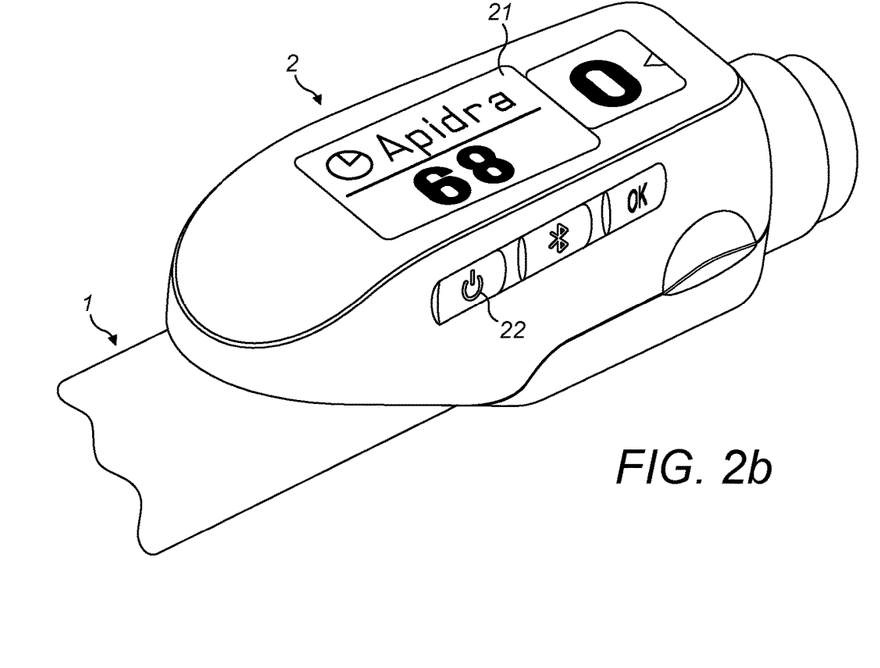
FIG. 2b: a perspective view of a supplementary device to be releasably attached to the drug delivery device of FIGS. 1a and 1b according to various aspects of the present disclosure.

FIG. 2b is a schematic illustration of a second embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
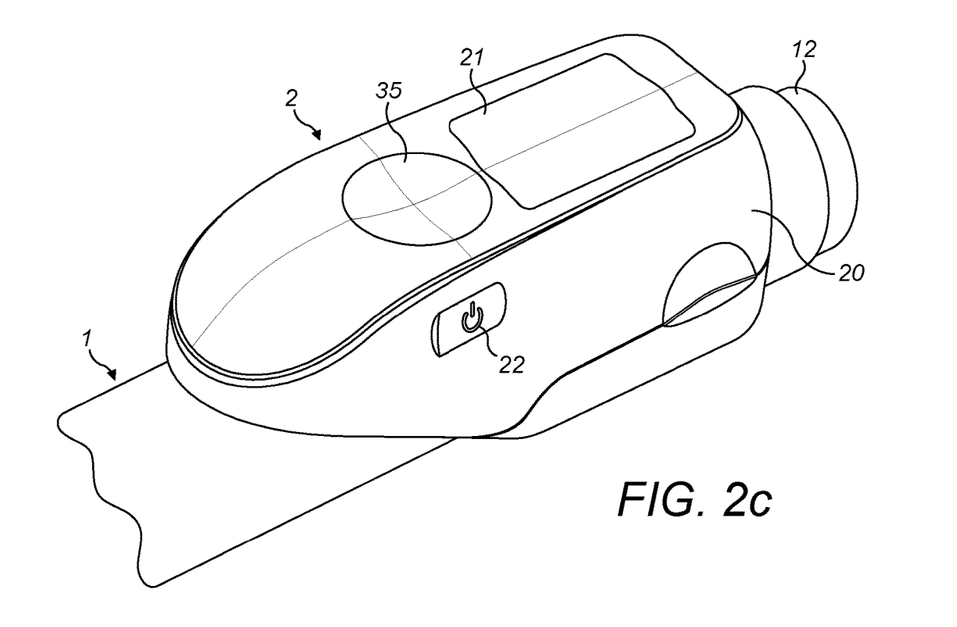
FIG. 2c: a perspective view of a supplementary device to be releasably attached to the drug delivery device of FIGS. 1a and 1b according to other aspects of the present disclosure.

FIG. 2c is a schematic illustration of a third embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3:
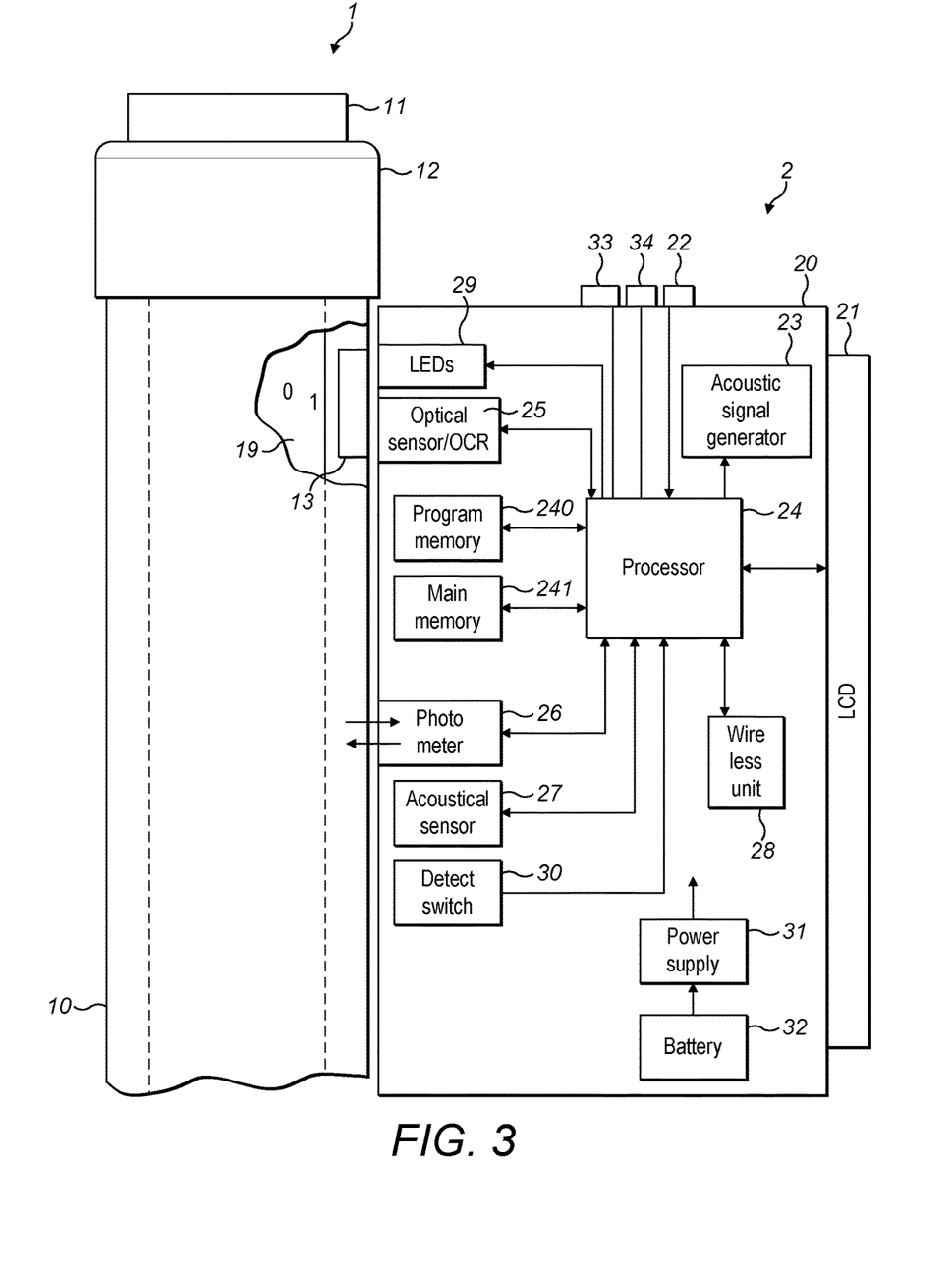
FIG. 3: a schematic view of a supplementary device attached to a drug delivery device showing components of the supplementary device.

FIG. 3 shows a schematic view of the supplementary device 2 of FIG. 2a in a state where it is attached to injection device 1 of FIG. 1.

With the housing 20 of supplementary device 2, a plurality of components are contained. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed (by way of numbers printed on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens system, for instance including two aspheric lenses. The magnification ratio (image size to object size ratio) may be smaller than 1. The magnification ratio may be in the range of 0.05 to 0.5. In one embodiment the magnification ratio may be 0.15.

Processor 24 further controls a photometer 26, that is configured to determine an optical property of the housing 10 of injection device 1, for example a color or a shading. The optical property may only be present in a specific portion of housing 10, for example a color or color coding of sleeve 19 or of an insulin container comprised within injection device 1, which color or color coding may for instance be visible through a further window in housing 10 (and/or in sleeve 19). Information on this color is then provided to processor 24, which may then determine the type of injection device 1 or the type of insulin contained in injection device 1 (e.g. SoloStar Lantus with purple color and SoloStar Apidra with blue color). Alternatively, a camera unit may be used instead of photometer 26, and an image of the housing, sleeve or insulin container may then be provided to processor 24 to determine the color of the housing, sleeve or insulin container by way of image processing. Further, one or more light sources may be provided to improve reading of photometer 26. The light source may provide light of a certain wavelength or spectrum to improve color detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance a expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fiber connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1. A battery 32 powers the processor 24 and other components by way of a power supply 31.

The supplementary device 2 of FIG. 3 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 4:
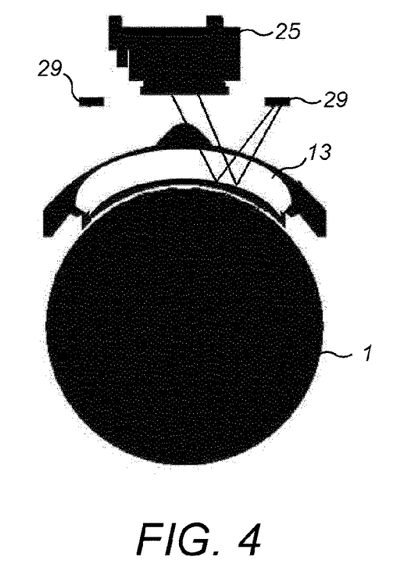
FIG. 4: a schematic illustration of the injection device and supplementary device showing reflections from a dose window of the injection device.

FIG. 4 shows schematically a cross-section of the injection device 1 and components of the supplementary device 2, including an exemplary position of the LEDs 29 (also referred to herein as illumination sources) with respect to the optical sensor 25 and dose window 13. FIG. 4 also illustrates the problem caused by reflections from the surface of the dose window 13. Due to manufacturing requirements and costs considerations, the dose window 13 is not usually made of a highly non-reflective material or provided with a non-reflective coating. The dose window may be made of a clear Polycarbonate. Therefore some of the light incident on the dose window 13 will be reflected from the dose window 13, rather than passing through to be incident on the number sleeve 19. In particular, it can be seen that light emitted from the LEDs 29 may be reflected from the lower surface of the dose window 13 towards the optical sensor 25 without reaching the number sleeve 19 of the injection device 1. These reflections lead to glare in the image captured by the optical sensor 25. As the LEDs 29 are point light sources, this glare generally takes the form of bright spots. The glare leads to areas of over exposure and impacts the ability of the optical sensor 25 to capture a high quality image of the numbers printed on the number sleeve 19, which in turn affects the ability of the processor 24 to perform a successful optical character recognition process on the numbers. It can be particularly hard to avoid glare in the captured image because the dose window 13 is curved and so the light is incident on the dose window 13 over a range of angles. LEDs 29 are the preferred choice of illumination because of their small size and cost and their radiation characteristics. However, an alternative source, such as a light bulb, diode laser or an organic LED may be used.

The supplementary device 2 may also comprise a protection window (not shown). The primary function of the protection window is to seal the supplementary device 2 and prevent the ingress of dust and debris. However the protection window may also be shaped to provide magnification and/or focusing for the optical sensor 25.

Figure 5A:
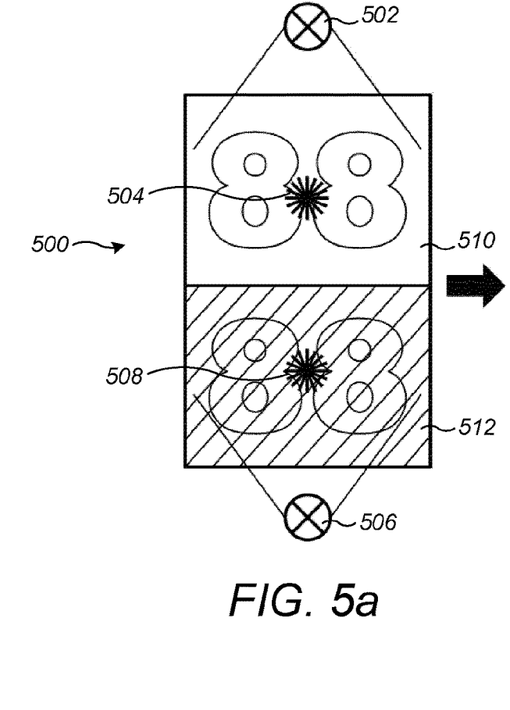
FIG. 5a: a first embodiment of a typical field of view of an optical sensor of the supplementary device, showing the position of LEDs and resulting reflections.

FIG. 5*a* shows a typical field of view 500 of the optical sensor 25. In general the field of view of the optical sensor 25 is large enough to capture an image of the entire dose window 13. In this embodiment the supplementary device 2 is provided with two LEDs 29 located above and below the dose window 13. When the upper LED 502 is activated, a first reflection 504 is seen by the optical sensor 25. When the lower LED 506 is activated, a second reflection 508 is seen by the optical sensor 25. Thus if both the upper and lower LEDs 502, 506 are activated, the optical sensor 25 sees two reflections in its field of view 500. If the reflections are located over a number, then they negatively impact the ability of the optical sensor 25 to capture a high quality image of these numbers. This can make it difficult to perform an accurate OCR process on the captured image, since information about the numbers has effectively been erased through over exposure.

It should be noted that the number 88 is used in this exemplary embodiment and in other embodiments described herein. In general this number occupies the greatest amount of space and is therefore the best candidate for assessing whether the reflections from the dose window 13 are located over the numbers. The skilled person will appreciate that the numbers printed on the number sleeve 19 represent a dose of medicament dialed into the injection device 1 and will therefore be sequential. For example, the numbers printed on the number sleeve 19 may be ascending even numbers. In some embodiments, the maximum dose which can be dialed into the injection device 1 is 80 units.

In order to eliminate the negative effects of the reflections 504, 508 on the image capture and decoding processes, there is provided a system and method in which multiple images of the number sleeve 19 are captured by the optical sensor 25 under different illumination conditions. These images are then combined to create a final image which is free from reflections. In the embodiment of FIG. 5*a*, the processor 24 is configured to divide images captured by the optical sensor 25 into two halves. The processor 24 is configured to control activation and deactivation of the upper and lower LEDs 502, 506 and to control the image capture process of the optical sensor 25.

Figure 5B:
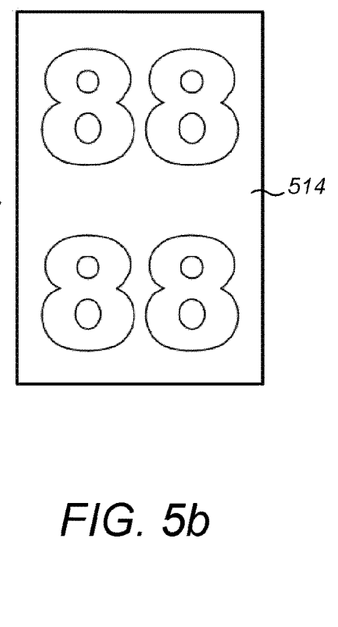

The processor 24 first activates the upper LED 502, which in general causes a first reflection 504 from the dose window 13. The processor 24 controls the optical sensor 25 to capture an image of the number sleeve 19. The processor 24 then discards the upper half 510 of this image and keeps only the lower half 512 of the image. Due to the position of the upper LED 502 relative to the optical sensor 25 no reflections are seen in the lower half 512 of the captured image. The processor 24 then deactivates the upper LED 502 and activates the lower LED 506. The processor 24 again controls the optical sensor 25 to capture an image of the number sleeve 19. In this second image the second reflection 508 in the lower half 512 is visible, but the first reflection 504 does not appear. Thus the processor 24 keeps the upper half 510 of this second image and discards the lower half 512. The processor 24 then executes an algorithm to combine the lower half 512 of the first image and upper half 510 of the second image to create a final image 514, illustrated in FIG. 5*b*. In practice, the image halves captured in the first and second images may overlap. This may be done to ensure that no image information is lost. The processor 24 may execute software which uses edge detection techniques to determine the appropriate place in each image for the combination to occur. The processor 24 then passes the final image 514 to an optical character recognition module, or performs the OCR process itself in order to identify the numbers visible in the image. OCR techniques are in general well known, and the skilled person will be aware of a number of OCR methods which could be applied in aspects of this disclosure.

Figure 6A:
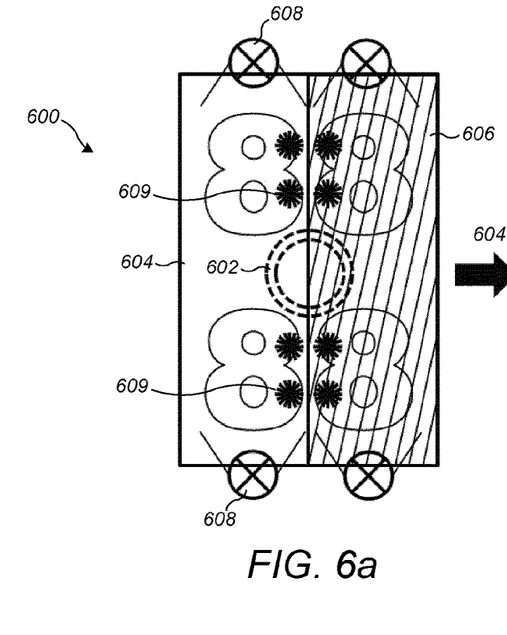
FIGS. 6a and 6b: a second embodiment of a field of view of an optical sensor of the supplementary device, showing the position of LEDs and resulting reflections.
Figure 6B:
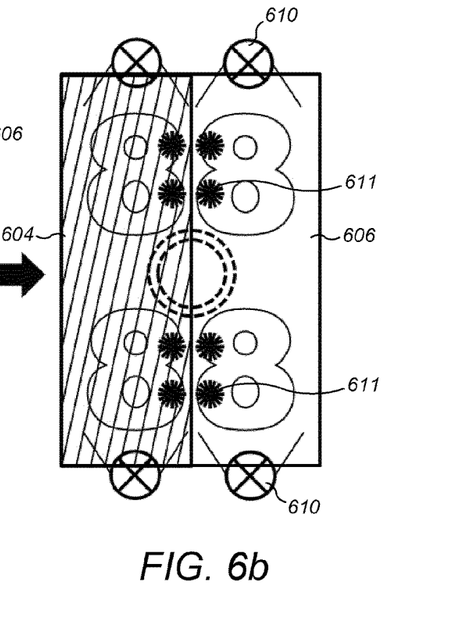

FIGS. 6*a* and 6*b* illustrate a second embodiment of the disclosure. In this embodiment the supplementary device 2 comprises four LEDs 29, arranged in pairs above and below the dose window 13. The position of the lens of the optical sensor is indicated by the dashed circle 602. As can be seen in these figures, the LEDs are located closer to the dose window 13 than in the first embodiment. Due to the relative position of the LEDs and optical sensor 25, each LED produces two reflections from the dose window 13 which are within the sensor's field of view 600.

In this embodiment the processor 24 divides the field of view of the optical sensor 25 vertically, into a left half 604 and a right half 606. The processor 24 controls the LEDs to be activated in left and right pairs. The processor 24 first activates the left LEDs 608. This causes reflections 609 to appear on the left half 604 of the field of view of the optical sensor 25. The processor 24 controls the optical sensor 25 to capture an image of the number sleeve 19. The processor 24 discards the left half 604 of this image and keeps the right half 606 of the image. This is illustrated in FIG. 6*a* by the cross hatching in the right half 606 of the field of view 600. The next step is illustrated in FIG. 6*b*, in which the processor 24 deactivates the left LEDs 608 and activates the right LEDs 610. This causes reflections 611 to appear in the right half 606 of the field of view sensor. The processor 24 again controls the optical sensor 25 to capture an image of the number sleeve 19. The processor 24 discards the right half 606 of this second image and keeps the left half 604 of the image (this is again illustrated by cross hatching in the left half 604). The processor 24 then takes the right half 606 of the first image and left half 604 of the second image and combines them into a final image which is free of reflections.

Having a greater number of LEDs 29 increases the quality and evenness of the illumination. Positioning the LEDs 29 closer to the dose window 13 also improves the illumination of the number sleeve 19 and increases the amount of light reaching the dose window 13 and optical sensor 25 for a given LED light output. In general, it is desirable to position the LEDs 29 such that minimal reflections appear in the illuminated area, while at the same time producing an illumination which is bright and homogeneous. Thus the LEDs 29 are positioned such that the reflections produced appear in a section of the field of view and captured image which is subsequently discarded. Dividing the field of view vertically into left and right halves, rather than upper and lower halves also increases the quality of the illumination as the part of the image which the processor 24 keeps is closer to a source of illumination. Another advantage of certain aspects of the disclosure is that they require no modification of existing injection pen designs to implement.

Figure 7A:
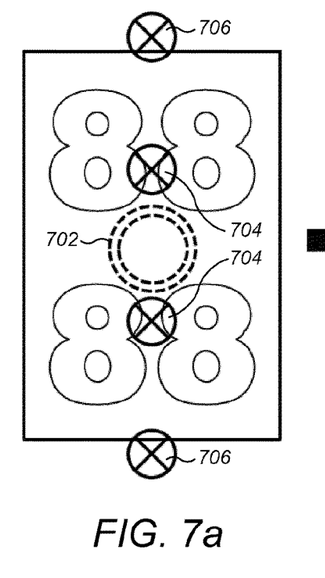
FIGS. 7a and 7b: a third embodiment of a field of view of an optical sensor of the supplementary device, showing the position of LEDs and resulting reflections.
Figure 7B:
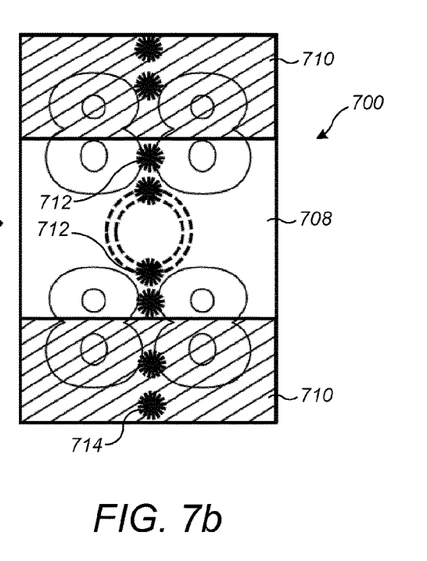

FIGS. 7*a* and 7*b* show a third embodiment of the disclosure. In this embodiment there are again four LEDs 29 arranged linearly along a center line of the dose window 13. The lens position 702 is again illustrated with a dashed circle. In this embodiment the LEDs are grouped into an inner pair 704 and an outer pair 706. The inner pair 704 are located approximately one third of the dose window 13 height from the top and bottom edges of the dose window 13. The outer LEDs 706 are located at the dose window 13 edges.

In this embodiment the processor 24 divides the field of view 700 into a central section 708 and two peripheral sections 710. The central section 708 may occupy approximately half of the field of view 700, while the peripheral section 710 each occupy approximately one quarter of the field of view. However these ratios may be adjusted depending on the expected positions of the reflections.

The processor 24 first activates the inner LEDs 704. This produces inner reflections 712 in the central section 708 of the field of view 700 of the optical sensor 25. The processor 24 controls the optical sensor 25 to capture an image of the number sleeve 19. The processor 24 keeps the upper and lower peripheral sections 710 of this image and discards the central section 708 of the image. The processor 24 then deactivates inner LEDs 704 and activates outer LEDs 706. These LEDs cause outer reflections 714 to appear in the upper and lower peripheral section 710 of the field of view 700. The processor 24 again controls the optical sensor 25 to capture an image of the number sleeve 19. The processor 24 keeps the central section 708 of this second image and discards the upper and lower peripheral section 710 of the image. The processor 24 then combines the upper and lower peripheral sections 710 from the first image with the central section 708 from the second image to create a final image which is free of reflections. An OCR process can then be performed on this final image to determine the numbers which are visible.

In some embodiments of the disclosure only even numbers are printed, in ascending order, on the number sleeve 19. In this case each of the arrangements shown in FIGS. 5*a* to 7*b* represents a situation in which an odd number of units are dialed into the injection device 1. This is because the number of dialed units would normally be displayed centrally within the dose window 13.

Figure 8:
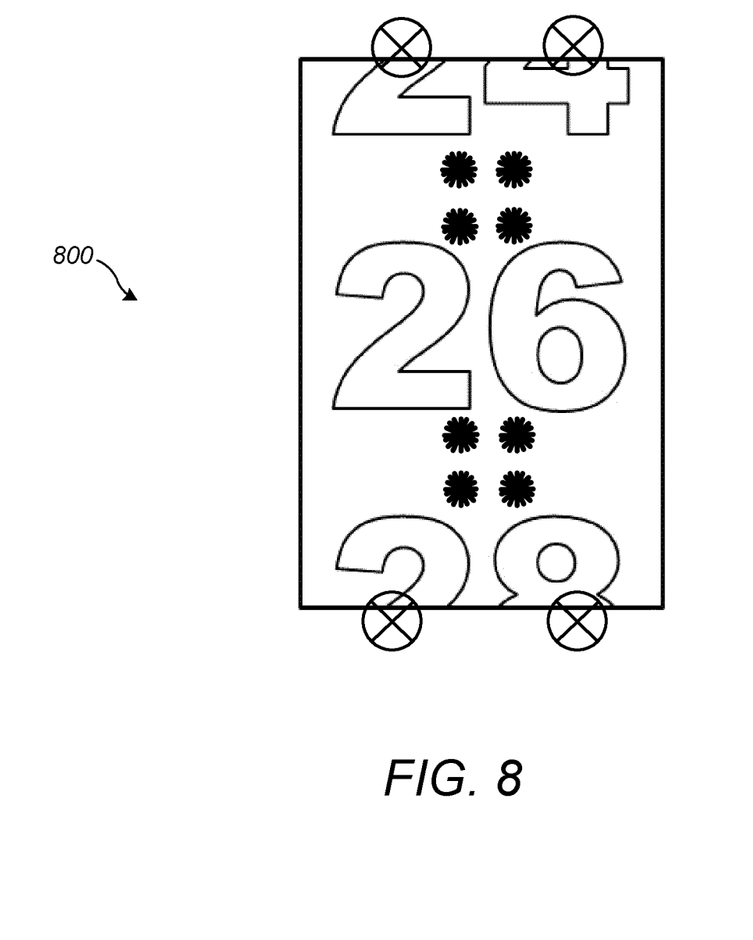
FIG. 8: an embodiment in which a number appears in the centre of the field of view of the optical sensor.

FIG. 8 illustrates an embodiment in which only even numbers are printed on the number sleeve 19 and where a dose of 26 units has been dialed into the injection device 1. Thus the number 26 appears centrally in the dose window 13. The position of the LEDs 29 in FIG. 8 is the same as in FIGS. 6a and 6b, with a pair of LEDs located at either end of the dose window 13. The optical sensor lens is again located centrally above the dose window 13. This arrangement of LEDs therefore leads to the same pattern of reflections in the field of view 800 of the optical sensor 25. However since these reflections occur in the upper and lower thirds of the field of view 800, none of the reflections directly overlap with the centrally displayed number. Thus no division of the field of view 800 by the processor 24 is necessary in this situation. Alternatively, the processor 24 may continue to divide the image as previously described, even if the reflections do not obscure any areas of interest. The processor 24 may additionally be configured to detect the white spaces between the printed numbers in order to determine whether a number is displayed centrally within the window or not.

The invention claimed is:

1. A supplementary device for attachment to an injection device, the supplementary device comprising:
an imaging device configured to capture an image of a moveable number sleeve of the injection device;
a plurality of light sources comprising a first group of light sources and a second group of light sources; and
a processor configured to control operation of the imaging device and plurality of light sources and to receive image data from the imaging device,
wherein the processor is configured to:
activate the plurality of light sources sequentially by being configured to activate the first group of light sources followed by the second group of light sources;
capture a first image of the moveable number sleeve when the first group of light sources are activated;
capture a second image of the moveable number sleeve when the second group of light sources are activated;
divide the field of view of the imaging device into a central section and two peripheral sections and to associate the central section with a first illumination condition and the two peripheral sections with a second illumination condition; and
combine the first image of the moveable number sleeve and the second image of the moveable number sleeve into a single image.

2. The supplementary device according to claim 1, wherein the supplementary device comprises four light sources grouped into first and second pairs and wherein the processor is configured to activate the plurality of light sources sequentially by being configured to activate the first pair of light sources followed by the second pair of light sources.

3. The supplementary device according to claim 1, wherein the processor is configured to keep the two peripheral sections of the first image and discard the central section of the first image and to keep the central section of the second image and discard the two peripheral section of the second image.

4. The supplementary device according to claim 1, wherein each illumination source, when activated, results in one or more reflections from a transparent window of the injection device being visible in a field of view of the imaging apparatus.

5. A system comprising:
a supplementary device comprising:
an imaging device configured to capture an image of a moveable number sleeve of the injection device,
a plurality of light sources comprising a first group of light sources and a second group of light sources, and
a processor configured to control operation of the imaging device and plurality of light sources and to receive image data from the imaging device, wherein the processor is configured to:
activate the plurality of light sources sequentially by being configured to activate the first group of light sources followed by the second group of light sources;
capture a first image of the moveable number sleeve when the first group of light sources are activated;
capture a second image of the moveable number sleeve when the second group of light sources are activated;
divide the field of view of the imaging device into a central section and two peripheral sections and to associate the central section with a first illumination condition and the two peripheral sections with a second illumination condition; and
combine the first image of the moveable number sleeve and the second image of the moveable number sleeve into a single image; and
an injection device comprising:
a moveable number sleeve, the injection device being configured to have the supplementary device attached thereto.

6. A method of operating a supplementary device for attachment to an injection device, the supplementary device having an imaging device configured to capture an image of a moveable number sleeve of the injection device, a plurality of light sources comprising a first group of light sources and a second group of light sources and a processor configured to control operation of the imaging device and the plurality of light sources, the method comprising:
activating the first group of light sources followed by the second group of light sources;
capturing a first image of the moveable number sleeve when the first group of light sources are activated;
capturing a second image of the moveable number sleeve when the second group of light sources are activated;
receiving image data from the imaging device;
dividing the field of view of the imaging device into a central section and two peripheral sections and to associate the central section with a first illumination condition and the two peripheral sections with a second illumination condition; and
combining the first image of the moveable number sleeve and the second image of the moveable number sleeve into a single image.

* * * * *